United States Patent [19]

Itoh et al.

[11] 4,313,001
[45] Jan. 26, 1982

[54] PROCESS FOR PURIFYING AQUEOUS ACRYLAMIDE SOLUTIONS

[75] Inventors: Hiroshi Itoh, Yokohama; Tadatoshi Honda, Fujisawa; Jun Saitoh, Kamakura; Takatoshi Mitsuishi, Isehara, all of Japan

[73] Assignee: Mitsui Toatsu Chemicals Incorporated, Tokyo, Japan

[21] Appl. No.: 186,057

[22] Filed: Sep. 11, 1980

[30] Foreign Application Priority Data

Sep. 13, 1979 [JP] Japan .............................. 54-116776
Jan. 28, 1980 [JP] Japan ................................ 55-7726

[51] Int. Cl.$^3$ ....................................... C07C 103/133
[52] U.S. Cl. .................................................. 564/206
[58] Field of Search ........................................ 564/206

[56] References Cited

U.S. PATENT DOCUMENTS

| | | | |
|---|---|---|---|
| 2,865,960 | 12/1958 | Shearer, Jr. et al. | 564/206 |
| 3,923,741 | 12/1975 | Asano et al. | 564/206 |
| 4,108,893 | 8/1978 | Asano et al. | 564/206 |

Primary Examiner—Thomas A. Waltz

[57] ABSTRACT

A process for purifying an aqueous acrylamide solution which has been obtained through catalytic hydration of acrylonitrile in the presence of a copper-containing catalyst, by the steps of passing said solution through a OH-form strongly basic anion exchange resin layer and then, through a H-form cation exchange resin layer, is disclosed.

3 Claims, No Drawings

PROCESS FOR PURIFYING AQUEOUS ACRYLAMIDE SOLUTIONS

BACKGROUND OF THE INVENTION (1) Field of the Invention

This invention relates to an improvement in the purification process of an aqueous acrylamide solution which has been obtained by catalytically hydrating acrylonitrile with water in the presence of a copper-containing catalyst. The invention particularly relates to a process for the preparation of aqueous acrylamide solutions which are useful as the starting material of high molecular weight flocculant.

(2) Description of the Prior Arts

Acrylamide is valuable as the starting material of acrylamide polymer which has versatile utilities such as paper-reinforcing agent and high molecular weight flocculant. The preparation of acrylamide has become relatively simple, as the conventional sulfuric acid process is replaced by catalytic hydration of acrylonitrile in the presence of a catalyst composed chiefly of copper metal. According to the latter process, the acrylamide is obtained as an aqueous solution, and can be advantageously fed directly into the polymerization reaction system. When the aqueous acrylamide solutions obtained upon such hydration are immediately subjected to polymerization, however, acrylamide polymers having high performance of flocculation and solubility cannot be obtained. Not only that, in extreme cases the polymerization reaction itself fails to progress.

Presumably such phenomena are caused by the various impurities present in the aqueous acrylamide solution in minor amounts due to the method of preparing said solution, which adversely affect the polymerization reaction. Such impurities would include unreacted acrylonitrile, metal ions such as of copper eluted from the catalyst component, the impurities in the starting acrylonitrile and the side products such as organic acid. Of the above-named, unreacted acrylonitrile can be easily removed by conventional means such as distillation. Also the metal ions such as of copper can be easily removed by a treatment with cation exchange resin. Even after the distillation for removing unreacted acrylonitrile and the cation exchange resin treatment, the aqueous acrylamide solution cannot serve as a satisfactory starting material for a high molecular weight flocculant having a high performance of flocculation and water-solubility, although it may be satisfactory for making a paper-reinforcing agent.

That is, when acrylamide is used as a paper-reinforcing agent, acrylamide polymers of relatively low molecular weight, such as in the order of several ten thousands, can be used. When it is to be used as a high molecular weight flocculant, normally high molecular weights such as several millions are required. Recently acrylamide polymers of super high molecular weight such as above ten millions are manufactured for this purpose. Furthermore, with the increase in variety and degree of complication of industrial waste waters, various types of high molecular weight flocculants are produced, i.e., not only their molecular weights are drastically increased, but some are imparted with anionic property through the hydrolysis of amide groups in the polymers, or others are caused to contain monomers other than acrylamide through copolymerization.

Accompanying such increased versatility and improved performance of high molecular weight flocculants, the starting acrylamide also is required to have improved quality, and hence the heretofore permitted very minor amounts of impurities must now be removed.

As the means to remove impurities from the aqueous acrylamide solutions prepared by conventional sulfuric acid process, their treatment first with cation exchange resins and then with anion exchange resins was proposed in *J. Appl. Chem.* of U.S.S.R. vol. 41, p. 820 (1968). Also concerning the aqueous acrylamide solutions obtained by the catalytic hydration, a purification method of treating them with OH- or weak acid salt-form, strongly basic anion exchange resin is disclosed in Japanese Laid-Open Patent Application, Publication No. 82011/75. Furthermore, the process of treating the latter solutions with a mixed bed composed of a cation exchange resin and an anion exchange resin is known from Japanese Laid-Open Patent Application, Publication No. 83323/75.

As has been disclosed, for example, in Japanese Laid-Open Patent Applications, Publication Nos. 66618/79, 73727/79 and 74890/79, however, ordinary ion-exchange resin treatments fail to remove certain impurities depending on their structures. In order to cope with the shortcoming, the named prior arts proposed respectively to add ammonia, urea or the like to the catalytic hydration reaction system, to add to said system a meta-substituted phenolic compound, or to apply a unique polymerizing method to the aqueous acrylamide solutions.

Our research works also proved that the aqueous acrylamide solutions treated with an OH-form, strongly basic anion exchange resin, or with a weak acid salt form strongly basic anion exchange resin, or with the aforesaid mixed bed, failed to polymerize under certain polymerization conditions, or if polymerized, failed to serve as the starting material of a high molecular weight flocculant having excellent performance of flocculation and solubility in water. A number of causes may be enumerated for such phenomena. Our studies disclosed that, the bifunctional vinyl monomers such as methylene bis-acrylamide, which are present in acrylamide as the impurities, are incorporated into the polymer chain of the polyacrylamide during the polymerization reaction, rendering the polymer to have a branched structure, not the straight chain. Such a branched polymer is less effective than the straight chain polymer as a high molecular weight flocculant. Hence, it must be added to the waste water to be treated by an increased amount. Not only that, the turbidity of the treated waste water cannot be sufficiently improved. Thus the flocculant fails to achieve satisfactory results. If the molecular weight of the acrylamide polymer is increased in an attempt to reduce its amount of addition to the waste water, the polymer having such a branched structure shows poor solubility, failing to function as a flocculant.

SUMMARY OF THE INVENTION

The primary object of this invention is to provide a process for purifying the aqueous acrylamide solution obtained upon catalytically hydrating acrylonitrile in the presence of a copper-containing catalyst, to the level satisfactory as the starting material of polyacrylamide.

Another object of the invention is to provide the aqueous acrylamide solution which is useful as the starting material for high molecular weight flocculant exhibiting excellent performance of flocculation as well as the solubility in water.

According to the subject process, the above first and second objects are achieved by passing the aqueous acrylamide solution obtained through the catalytic hydration of acrylonitrile in the presence of a copper-containing catalyst, first through a OH-form strongly basic anion exchange resin layer, and then through a H-form cation exchange resin layer. With the solution purified according to the subject process, the polymerization smoothly proceeds under the polymerization conditions under which the product of conventional purification process, i.e., the treatment with a OH-form strongly basic anion exchange resin alone, cannot be polymerized. Furthermore, high quality aqueous acrylamide solutions such as those never obtainable through the known processes can be easily obtained.

DETAILED DESCRIPTION OF THE PREFERRED EMBODIMENTS

For practicing the subject invention, the following scheme was invented. That is, heretofore no means of measuring the branching ratio of water-soluble polymers such as acrylamide polymer is known. We discovered a method of determining the branching ratio, which comprises hydrolyzing the amide groups in a polyacrylamide and comparing the rise ratio in intrinsic viscosity of the polymer before and after the hydrolysis, with the standard value. We furthermore examined the correlation between the branching ratio of a polymer with its flocculation performance. We thus confirmed, as is also apparent from the results of later given Examples 1–4 and Control 1, that the rise ratio in the intrinsic viscosity of the polyacrylamide produced from the acrylamide, which has been purified by the subject process, is equivalent to that of the polyacrylamide produced from the acrylamide which has been purified by repetitive crystallization; and also that the polyacrylamide has a straight chain structure with a low branching ratio. Incidentally, the polyacrylamide produced from the crystalline acrylamide which had been purified by repetitive crystallization, shows excellent flocculation performance and water-solubility.

Hereinafter the invention will be explained in further details.

The aqueous acrylamide solutions to which the present invention is to be applied are those obtained by catalytically hydrating acrylonitrile in the presence of copper-containing catalysts. As the copper-containing catalyst to be used in said production of acrylamide, many different types have been proposed, and any of which are useful for the present invention.

For example, those copper metal or the catalysts containing copper metal can be used, such as (1) copper in the form of wire or powder, and copper ion (2) reduced copper obtained by reducing copper compounds such as copper oxide, copper hydroxide and copper salts, with hydrogen or carbon monoxide, at such high temperatures as 100°–400° C., (3) reduced copper obtained by reducing copper compounds such as copper oxide, copper hydroxide and copper salts, with such reducing agents as hydrazine, borohydrides of alkali metals or alkaline earth metals, and formaldehyde, in the liquid phase, (4) reduced copper obtained by treating copper compounds such as copper oxide, copper hydroxide and copper salts in the liquid phase, with the metals having greater ionizing tendency than copper, such as zinc, aluminium, iron, tin and the like, (5) Raney copper obtained by developing Raney alloys composed of copper and other metals such as aluminium, zinc and magnesium, (6) copper metal obtained by pyrolyzing an organic complex compound such as copper formate or oxalate, at such temperature ranges as 100°–400° C., and (7) pyrolyzate of copper hydride. Those copper-containing catalysts may contain, besides the normally used carriers, conventionally employed metals other than copper, such as chromium or molybdenum.

The reaction of acrylonitrile with water in the presence of such a copper-containing catalyst as described above is effected normally using practically optional amount of water to the acrylonitrile, at the temperatures ranging from 50°–150° C., preferably 80°–135° C., under atmospheric or elevated pressure, on the catalyst bed which may be suspended or fixed, either continuously or batchwise, in the liquid phase, while preventing the contact of the reaction material and the copper-containing catalyst, with oxygen or an oxygen-containing gas.

Then the resulting reaction liquid is distilled so that its unreacted acrylonitrile content should be removed, preferably reduced to no more than 300 ppm, and also that it may be concentrated to an acrylamide content of 30–50% by weight. Under the above-described reaction conditions, the formation of decomposition products of acrylonitrile during the subsequent purification steps and the removal of the decomposition products are facilitated.

Thus obtained aqueous acrylamide solution is then treated in accordance with the invention. That is, the solution is passed, first through a OH-form strongly basic anion exchange resin layer, and then through a H-form cation exchange resin layer.

The contact of the aqueous acrylamide solution with the resins is effected by any of fixed bed, suspended bed or moving bed system, while normally a fixed bed being employed. The solution may be passed as an up-flow or a down-flow. The temperature range suitable for passing the solution is such that at which no degeneration of acrylamide takes place, and no crystalline acrylamide is precipitated, i.e., normally not higher than 60° C.

The ion-exchange resins to be used in this invention can be selected from the commercialized conventional products. As the strongly basic anion exchange resin, for example, Amberlite IRA-402 (product of Rohm and Haas Co., tradename), Diaion PA-416 (product of Mitsubishi Kasei Kogyo K.K., tradename) and Lewatit MP-500 (product of Bayer AG, tradename) may be named. Whereas, the cation exchange resin may be strongly acidic or weakly acidic, specific examples including Amberlite IR-120B (product of Rohm and Haas Co., tradename), Diaion WK-10 (product of Mitsubishi Kasei Kogyo K.K., tradename) and Lewatit CNP-80 (product of Bayer AG, tradename). It should be noted that the concept of "strongly basic anion exchange resin" referred to in this specification includes the so-called medium basic anion exchange resins, such as Lewatit MP-64 (product of Bayer AG, tradename) containing concurrently tertiary amine and quaternary ammonium as the functional groups having the anion exchange ability.

The strongly basic anion exchange resins are generally used in OH- or weak acid salt-form, and rarely in strong acid salt-form. Whereas, the cation exchange resin is normally used in H-form or weakly basic salt form, and rarely in strongly basic salt form. According to the present invention, however, it is essential that they should be used in OH-form and H-form, respectively. If they are used with the ionic forms other than the specified, the purification effect achievable with the subject process cannot be expected, as is clear also from the result of later given Controls.

Preceding the ion exchange resin treatment of the aqueous acrylamide solution according to the present invention, it is preferred to remove at least a part, preferably at least more than half, of the copper ions and other cationic substances contained in said crude aqueous acrylamide solution as obtained from the catalytic hydration of acrylonitrile, by a treatment with a cation exchange resin as already described. Such a pre-treatment prevents the precipitation of copper compound within the ion-exchange resin layer, and facilitates the stable purification operation of the subject process. It is particularly effective for lengthening the life of the H-form cation exchange resin layer used for the subsequent treatments of the solution.

It also produces a favorable effect to contact the crude aqueous acrylamide solution with oxygen or an oxygen-containing gas, or to treat the solution with a weakly basic anion exchange resin to remove the anionic impurities, in advance of the ion-exchange resin treatment according to the subject process.

In one of the embodiments, the process of this invention may be practiced as a pre-treatment of acrylamide polymer preparation. As the polymerization initiator to be used in the polyacrylamide preparation in such an embodiment, any of azo compounds and/or organic peroxides or inorganic peroxides and reducing agents can be used. Many known compounds can be named as such polymerization initiators, e.g., azo compounds such as azobisdimethylvaleronitrile, sodium salt of azobiscyanovaleric acid, azobis-isobutyronitrile and azobis-aminopropane hydrochloride; organic peroxides such as benzoyl peroxide, lauroyl peroxide, and tertiary butyl hydroperoxide; inorganic peroxides such as potassium persulfate, sodium perbromide, ammonium persulfate and hydrogen peroxide; inorganic reducing agents such as ferrous sulfate, ferrous chloride, sodium bisulfite, sodium metasulfite, sodium thiosulfate and nitrite; and organic reducing agents such as dimethylaniline, 3-dimethylaminopropionitrile and phenyl hydrazine.

Also in such an embodiment, the monomeric component used for producing a high molecular polymer is either acrylamide alone or a mixture of acrylamide with other copolymerizable monomer or monomers. As the monomers copolymerizable with acrylamide, for example, methacrylamide, acrylic acid or salts thereof, N-methylacrylamide, N,N'-dimethylacrylamide, N-methylolacrylamide, 2-acrylamide-2-methylpropane sulfonic acid or salts thereof, amino alcohol esters of methacrylic acid or acrylic acid (for example, dimethylaminoethyl-methacrylate, diethylaminoethyl-acrylate and the like), their salts or quaternary ammonium salts; and ester compounds of methacrylic acid or acrylic acid (for example, methyl methacrylate and hydroxyethyl acrylate) and acrylonitrile may be named.

Hereinafter the invention will be explained with reference to the working examples.

EXAMPLE 1

Preparation of a crude aqueous acrylamide solution:

A reactor was charged with 70 parts by weight of Raney copper and 1000 parts of a 25 wt. % aqueous acrylonitrile solution. The reaction was performed at 110° C. for 10 hours. Thereafter the catalyst in the reaction liquid was removed by filtration, and the filtrate was passed through a reduced pressure distillator to be removed of the unreacted acrylonitrile and a part of water. Thus an aqueous acrylamide solution with a concentration of 33 wt. % was obtained. This crude aqueous acrylamide solution contained no more than 300 ppm of acrylonitrile and no more than 80 ppm of copper. Purification of the aqueous acrylamide solution:

Two 50-cm long glass ion exchange columns having an inner diameter of 20 mm each (columns A, B) were prepared. The column A was filled with 100 ml of a strongly basic anion exchange resin, Lewatit MP-500 (product of Bayer AG) which was rendered OH-form; and the column B, with 100 ml of a strongly acidic cation exchange resin, Amberlite IR-120B (product of Rohm and Haas Co.) which had been regenerated to H-form and washed thoroughly with water.

The two columns were disposed in series as A-B, and through which the aforesaid aqueous acrylamide solution was passed at a space velocity (SV) of 3 (300 ml/hr.), and 0.96 m/hr., respectively.

Preparation of the polymer:

Thus obtained aqueous acrylamide solution was diluted to have an acrylamide concentration of 20% by weight with distilled water. An aqueous caustic soda solution was blown into 100 parts of the solution to adjust the latter's pH to 10. Nitrogen was blown into the solution to purge the dissolved oxygen outside the system. Maintaining the system at 30° C., potassium persulfate as the catalyst and nitrotrispropionamide as the promotor were added thereto in the amounts of, respectively, $8.0 \times 10^{-5}$ mol and $20.0 \times 10^{-5}$ mol, per mol of the acrylamide. The reaction was allowed to proceed with the temperature rise caused by the heat of polymerization. The system was allowed to stand for an additional hour after no more temperature rise was observed, to complete the polymerization reaction.

Thus a jelly-like product was obtained, which was crushed into the grains each having the diameter not greater than 2 mm. The water therein was substituted with methanol, and the jelly was then dried at 50° C. under a reduced pressure, to provide the powderized polymer.

The polymer evaluation:

The water-solubility, branching ratio and flocculation performance of the dry polymer as above-obtained were evaluated by the methods specified below. The results are given in Table 1.

(1) The water-solubility

The dry polymer was made into a 0.1 wt. % aqueous solution and passed through a 200-mesh filter cloth. The water-insoluble matter was recovered by the filtration, which was dried at 120° C. and weighed to determine the weight percent of the water-insoluble matter.

(2) Branching ratio

To 100 g of the 0.1 wt. % aqueous polymer solution prepared in the above solubility test, 7 g of 0.1-N NaOH solution was added, and after thorough stirring, the mixture was left in a 80° C. aqueous bath for 3 hours, to effect hydrolysis. The intrinsic viscosities of the solutions before and after the hydrolysis were measured at 30° C. in 1-N sodium nitrate, to determine the rise ratio in the intrinsic viscosities before and after the hydrolysis.

(3) Flocculation performance

In this Example and the later given Examples 3-7 and Controls 2-10, a waste water (pH 6.0) formed by adding 400 ppm of alumina sulfate to a kraft pulp waste water was used for the test. To 300 ml of the waste water taken in a 500 ml-sealable cylinder, the dry polymer was added by 2 ppm by weight ratio. Mixing the system by turning the cylinder over five times, the size of the formed flock and the transmittance of the supernatant liquid (cell thickness, 1 cm) were measured.

Also, in Examples 8-9 and Controls 11-12, 300 ml each of the excess sludge suspension (pH 6.2; SS 3.4%) originated from an activated sludge treatment of waste water from paper industry was taken into a 500 ml-sealable cylinder, and to which the dry polymer obtained as above was added to a weight ratio of 10 ppm. Mixing the system by turning the cylinder over 5 times, the size of the flock formed and the water content of the dewatered cake obtained by centrifugal dewatering of the flock was determined by drying the cake at 105° C. for 10 hours and measuring its weight decrease.

EXAMPLE 2

During the purification of the aqueous acrylamide solution in Example 1, it was observed that, starting from 4 to 5 hours after the resin treatment began, the pressure difference at the entrance and exit of the column A gradually increased. In this Example, the crude aqueous acrylamide solution used in Example 1 was first passed through a column filled with 100 ml of a H-form cation exchange resin, Amberlite 120B (product of Rohm and Haas Co.) at SV3, and then purified in the identical manner with Example 1. The increase in pressure difference at the entrance and exit of the column A was not observed. Thus obtained purified aqueous acrylamide solution was polymerized in the similar manner to Example 1, and the polymer was evaluated of its water-solubility, branching ratio and flocculation performance.

EXAMPLE 3

The crude aqueous acrylamide solution prepared by the catalytic hydration as described in Example 1 was purified in the identical manner with that of Example 1, except that the column B was filled with a weakly acidic cation exchange resin, Lewatit CNP-80 (product of Bayer AG). The polymer obtained by polymerizing the purified aqueous acrylamide solution similarly to Example 1 was evaluated of its water-solubility, branching ratio and the flocculation performance.

EXAMPLE 4

Example 1 was repeated except that the column A was filled with an anion exchange resin having two types of anion exchange groups of tertiary amine and quaternary ammonium, Lewatit MP-64 (product of Bayer AG). The water-solubility, branching ratio and flocculation performance of the polymer were evaluated.

EXAMPLES 5-9

The acrylamide which had been prepared and purified by the procedures described in Example 1 was copolymerized with the copolymerizable monomers specified in Table 2 at the monomeric ratios also specified in Table 2, at pH 7, in the presence of ammonium persulfate as the catalyst and sodium bisulfite as the promotor, in the amounts of, respectively, $2.2 \times 10^{-5}$ mol and $1.0 \times 10^{-5}$ mol, per mole of the acrylamide. Otherwise the polymerization was performed similarly to Example 1. The water-solubility and the flocculation performance of the resulting copolymers were similarly evaluated.

Control 1

A 40 wt. % aqueous acrylamide solution was cooled to $-5°$ C., and the precipitated crystalline acrylamide was separated. Distilled water was added to the crystals to form a 50 wt. % aqueous acrylamide solution. The above cycle of operations was further repeated twice, to provide a purified acrylamide, which was polymerized similarly to Example 1. The water-solubility, branching ratio and the flocculation performance of the polymer were evaluated.

Controls 2-7

The crude aqueous acrylamide solution prepared by the procedures described in Example 1 was passed through the columns A and B filled with the ion exchange resins specified in Table 1, at the SV also specified in Table 1. Thus obtained aqueous acrylamide solutions were polymerized similarly to Example 1, and the water-solubility and flocculation performance of the resulting polymers were evaluated.

Controls 8-12

The crude aqueous acrylamide solution prepared by the method of Example 1 was passed through a mixed bed column composed of carbonate-form Lewatit MP-500 and H-form Amberlite IR-120B, at a SV of 1.5. Thus obtained aqueous acrylamide solution was copolymerized with the monomers specified in Table 2, at the monomeric ratios specified in the same table, in the manner similar to Examples 4-8. The water-solubility and the flocculation performance of the resulting polymers were duly evaluated.

TABLE 1

| | | Purification Method of Acrylamide | | | | | Polymer Evaluation | | | |
| | | Column A | | | Column B | | | Water-solubility | Branching ratio | Flocculation | Performance |
| | No. | Type of resin | Form of ion | SV | Type of resin | Form of ion | SV | Insoluble component (%) | Rise ratio intrinsic viscosity | Flock size (mm) | Light transmittance (%) |
|---|---|---|---|---|---|---|---|---|---|---|---|
| Example | 1 | Lewatit MP-500 | —OH | 3 | Amberlite 120B | —H | 3 | less than 0.1 | 1.92 | 4~5 | 68.4 |
| | 2 | " | —OH | 3 | Amberlite 120-B | —H | 3 | less than 0.1 | 1.92 | 4~5 | 70.1 |
| | 3 | " | —OH | 3 | Lewatit CNP-80 | —H | 3 | less than 0.1 | 1.93 | 4~5 | 70.3 |
| | 4 | Lewatit MP-64 | —OH | 3 | Amberlite 120B | —H | 3 | less than | 1.91 | 4~5 | 69.8 |

TABLE 1-continued

| | | Purification Method of Acrylamide | | | | | Polymer Evaluation | | | |
| | | Column A | | | Column B | | | Water-solubility Insoluble component (%) | Branching ratio Rise ratio intrinsic viscosity | Flocculation Flock size (mm) | Performance Light transmittance (%) |
|---|---|---|---|---|---|---|---|---|---|---|---|
| | No. | Type of resin | Form of ion | SV | Type of resin | Form of ion | SV | | | | |
| Control | 1 | | Recrystallization | | | | | 0.1 less than 0.1 | 1.95 | 4~5 | 71.0 |
| | 2 | Lewatit MP-500 | —CO₃ | 3 | Amberlite 120B | —H | 3 | 1.0 | 1.76 | 1~2 | 42.0 |
| | 3 | " | —OH | 3 | " | —NH₄ | 3 | Polymerization reaction failed to progress. | | | |
| | 4 | Lewatit MP-62 | —OH | 3 | " | —H | 3 | 1.6 | 1.71 | 1~2 | 40.5 |
| | 5 | Amberlite 120B | —H | 3 | Lewatit MP-500 | —OH | 3 | Polymerization reaction failed to progress. | | | |
| | 6 | Lewatit MP-500 | —OH | 3 | — | — | — | Polymerization reaction failed to progress. | | | |
| | 7 | Mixed bed of Lewatit MP-500 (—CO₃) and Amberlite 120B (—H) | | | | | 1.5 | 1.4 | 1.74 | 1~2 | 41.4 |

The classification of the resins named in the table was as follows:
Lewatit MP-500: strongly basic anion exchange resin
Lewatit MP-64: medium basic anion exchange resin
Lewatit MP-62: weakly basic anion exchange resin
Amberlite 120B: strongly acidic cation exchange resin
Lewatit CNP-80: weakly acidic cation exchange resin

TABLE 2

| | | Monomeric composition (mol %) | | Polymer Evaluation | | | |
|---|---|---|---|---|---|---|---|
| | | | | Water-solubility insoluble matter (%) | Flocculation performance | | |
| | No. | | | | Flock size (mm) | Light transmittance (%) | water content (%) |
| Example | 5 | AAM (95) | AA(5) | less than 0.1 | 4~5 | 70.2 | |
| | 6 | AAM (97) | MAM(3) | " | 4~5 | 73.1 | |
| | 7 | AAM (98) | AMPS(2) | " | 4~5 | 68.8 | |
| | 8 | AAM (90) | DM(10) | " | 5~7 | | 86.3 |
| | 9 | AAM (80) | DMg(20) | " | 6~8 | | 87.1 |
| Control | 8 | AAM (95) | AA(5) | 3.1 | 1~2 | 51.3 | |
| | 9 | AAM (97) | MAN(3) | 1.8 | 1~2 | 52.4 | |
| | 10 | AAM (98) | AMPS(2) | 1.2 | 1~2 | 49.8 | |
| | 11 | AAM (90) | DM(10) | 2.8 | 2~3 | | 89.7 |
| | 12 | AAM (80) | DMg(20) | 4.3 | 3~4 | | 91.3 |

The abbreviations of the monomers as given in the table respectively denote the following compounds.
AAM Acrylamide
AA Sodium acrylate
MAM N-methylolacrylamide
AMPS Sodium 2-acrylamide-2-methylpropane sulfonate
DM Methacryloyl-hydroxyethyl-dimethylamine sulfate
DMg Methacryloyl-hydroxyethyl-trimethyl ammonium chloride

What we claim is:

1. A process for purifying a crude aqueous acrylamide solution which has been obtained by catalytic hydration of acrylonitrile in the presence of a copper-containing catalyst, which comprises reducing unreacted acrylonitrile in said crude aqueous acrylamide solution to less than 300 ppm by distillation and then passing the thus reduced aqueous acrylamide first through a cation exchange resin layer, then through an OH-form strongly basic anion exchange resin layer, and ultimately through an H-form cation exchange resin layer.

2. The process according to claim 1 wherein said process is a pre-treatment in the preparation of a polyacrylamide polymer to be used as high molecular weight flocculant.

3. The process according to claim 1, wherein said first passing step of said solution through said cation exchange resin layer reduces copper ions contained in said solution to less than one half their original amount.

* * * * *